United States Patent [19]

Koezuka et al.

[11] Patent Number: 4,975,527

[45] Date of Patent: Dec. 4, 1990

[54] TISSUE-AFFINITIVE COLLAGEN FOR OSTEOGENESIS AND METHOD OF PRODUCING THE SAME

[75] Inventors: Masahiro Koezuka; Kunio Takaoka, both of Osaka; Kaneo Suzuki; Shigeo Yasugi, both of Nara, all of Japan

[73] Assignee: Nitta Gelatin, Inc., Osaka, Japan

[21] Appl. No.: 372,115

[22] Filed: Jun. 28, 1989

Related U.S. Application Data

[63] Continuation of Ser. No. 876,636, Jun. 20, 1986, abandoned.

[30] Foreign Application Priority Data

Jun. 21, 1985 [JP] Japan ............................ 60-136375

[51] Int. Cl.$^5$ .................. A61K 37/12; C07K 3/00; C07K 13/00
[52] U.S. Cl. .................. 530/356; 530/840; 514/21; 514/801; 435/68.1
[58] Field of Search .............. 530/356, 840; 514/21, 514/801; 128/DIG. 8; 424/95

[56] References Cited

U.S. PATENT DOCUMENTS

| | | | |
|---|---|---|---|
| 4,066,083 | 1/1978 | Ries | 530/356 |
| 4,314,380 | 2/1982 | Miyata et al. | 3/1.9 |
| 4,394,370 | 7/1983 | Jefferies | 424/15 |
| 4,563,350 | 1/1986 | Nathan et al. | 530/356 |

FOREIGN PATENT DOCUMENTS

| | | |
|---|---|---|
| 0132979 | 2/1985 | European Pat. Off. . |
| 2564732 | 11/1985 | European Pat. Off. . |
| 0182483 | 5/1986 | European Pat. Off. . |
| 0121976 | 7/1986 | European Pat. Off. . |
| 3147727 | 12/1980 | Fed. Rep. of Germany . |
| 2164042 | 3/1986 | United Kingdom . |

OTHER PUBLICATIONS

Chemical Abstracts vol. 93, 1980 No. 21, Nov. 24 p. 431 Abstract 903:201706d Yasui et al.

Physicochemical Characterization and Molecular Organization of of the Collagen A and B Chains, R. Kent Rhodes and Edward J. Miller 1978 American Chemical Society.

Die Angewandle Makromolekulare Chemie 111 (1983) 107-122 (NR. 1701), Collagen Heterogeneity and its Functional Significance, M. Z. Abedin and R. Riemschneider.

*Primary Examiner*—Nathan M. Nutter
*Attorney, Agent, or Firm*—Armstrong, Nikaido, Marmelstein, Kubovcik & Murray

[57] ABSTRACT

A good tissue-affinity and lack of antigenicity are required for the collagen used as the carrier of BMP. Conventional collagens have these properties only insufficiently. When the tyrosine content is below 2 residues/1000 residues, then the above properties of such collagens are good. Moreover, collagens excelling in the above properties can be readily obtained by using proteolytic enzymes.

3 Claims, 5 Drawing Sheets

TISSUE-AFFINITIVE COLLAGEN FOR OSTEOGENESIS AND METHOD OF PRODUCING THE SAME

This application is a continuation of application Ser. No. 876,636, filed June 20, 1986, now abandoned.

BACKGROUND OF THE INVENTION

This invention is related to the tissue-affinitive collagen used as carrier of bone morphogenetic protein and the method of producing the same.

Hitherto, when bone defect in a living body was to be filled, it was usual that autogeneous bone was removed from patient's own bone to be used for autogeneous bone grafts. This is because the process of incorporation of autogeneous bone grafts is earlier and more reliable than those of homogeneous or heterogeneous bone grafts. However, there are some such disadvantages to the use of autogeneous bone grafts as (1) the amounts of removed autogeneous bone is naturally limited, (2) removing autogeneous bone requires an additional surgical procedure on the same patient, heightening the risk of infection, extending the operating time, and leading to pain on the donor site. Therefore, when the bone defect is large, artificial biomaterials such as ceramics and metals have been used for bone graft substitutes. Such artificial biomaterials, however, can not readily be incorporated into surrounding bone tissue, because sufficient amounts of bone are not formed around the biomaterials.

To settle this problem, we have devised the use of osteoinductive biomaterials comprising a complex of collagen and bone morphogenetic protein or a composite of collagen, bone morphogenetic protein and tissue affinitive materials such as ceramics with a desired shape for filling and fixation of bone defects (J. P., A., No. 60-253455, U.S. Ser. No.737,386).

Both collagen and bone morphogenic protein (BMP) are known in the art and in the related literature Collagen has been well-established in the aspects of the chemistry, molecular structure, biochemical properties, and immunology, and enzyme-solubilized collagen is usually used as biomaterial because of the relatively low antigenicity (for example, U.S. Pat. No. 4,314,380). BMP was separated from Dunn osteosarcoma by Takaoka et al. (Biomedical Research 2: 466–471, 1981) and from bone tissue by Urist (U.S. Pat. No. 4,294,753). Jefferies (U.S. Pat. No. 4,472,840) demonstrated the method of inducing osseous formation by implanting bone graft material, which was prepared from both collagen and demineralized bone particles and/or bone morphogenic protein derived from bone.

We have prepared osteoinductive biomaterials using BMP which was separated from Dunn osteosarcoma and purified as described by Takaoka et al., and collagen, which was enzyme-solubilized collagen prepared by a conventional method, to study the osteogenic activity by implantation of the biomaterials into dorsal muscles of mice and found the following: On sole implantation of BMP, a large quantity of BMP, was required to induce ectopic bone formation, which was consistently observed when much less quantity of BMP was implanted in combination with collagen.

However, when enzyme-solubilized collagen prepared by a conventional method was used, the ectopic bone formation was not always induced smoothly, and the achievement was remarkably dependent on the amount of telopeptides in collagen used, which is closely related to the antigenecity of the collagen. Thus, when collagen containing less amount of telopeptides was used, the quantity of bone induced for a definite quantity of BMP implanted was increased, the minimum quantity of BMP required to induce ectopic bone formation was decreased, and higher reproducibility in the experiment was obtained. That is, collagen with lower antigenicity is required for more satisfactory induction of ectopic bone formation using BMP, and because of low yield of BMP when purified, the use of the collagen as carrier of BMP is also essential for the practical use.

Since the site of antigen of collagen exists mainly in non-helical terminal regions (telopeptides) of collagen molecule, a procedure to eliminate antigenicity has been taken through removal of the telopeptides of collagen molecule by allowing proteolytic enzymes, such as pepsin to act on collagen (for example, Int. Rev. Conn. Tiss. Res. 7. 61–99 (1976)).

OBJECT OF THE INVENTION

The object of this invention is to offer a collagen with good tissue affinity and without antigenicity and a method of producing the same.

BRIEF DESCRIPTION OF THE DRAWINGS

FIG. 2 enlarges part of tissue after osteogenesis was performed with collagen described in Example 1. FIG. 3 enlarges part of tissue after osteogenesis was performed with collagen stated in Reference example 1. FIG. 4 indicates the graft taken from a mouse.

DETAILED DESCRIPTION OF THE INVENTION

It has been well known that proteolytic enzymes other than collagenase digest selectively non-helical terminal regions (telopeptides) of collagen molecule to solubilize insoluble collagen, and major antigenic determinant of collagen locates in the telopeptides. Therefore, it has been also well known that collagen, either soluble or insoluble form, is treated with the enzymes to yield a telopeptide-poor collagen which is less antigenic than intact collagen. Commonly used method of obtaining the collagen from insoluble collagen source by enzyme treatment is as follows: Purified, de-haired animal hide or skin is cut to small pieces, dispersed in water with an appropriate pH to the enzyme used, and then treated with a proteolytic enzyme such as pepsin. After inactivating the enzyme, the resulting soluble collagen is recovered from the digest and further purified.

However, when collagen prepared in such a way was used as carrier of bone morphogenic protein derived from Dunn osteosarcoma, ectopic bone formation did not occur smoothly. We inventors considered: the failure of the ectopic bone formation using collagen obtained by such a conventional method was attributable to the fact that the digestion of telopeptides of the collagen used was not enough to show low antigenicity required to achieve ectopic bone formation, and the insufficient digestion was due to the presence of collagen polymer aggregates during digestion so that the enzyme did not act sufficiently on collagen and the antigenicity was not reached to low level adaptable to the ectopic bone formation.

We inventors performed following experiments to confirm the above idea: according to our findings, elimination of collagen polymer aggregates for obtaining collagen with low antigenecity level required for ectopic bone formation by the following enzyme treatment can be performed by, for example, filtration of solubilized collagen using membrane filters. Therefore, three kinds of collagen preparation, collagen solubilized with pepsin and not filtered with membrane filter (A), collagen solubilized with pepsin and filtered with a 0.45 μm membrane filter prior to inactivation by pepsin (B) and collagen solubilized with pepsin and filtered with the same after inactivation (C) were prepared to measure molecular distribution and amino acid composition, and the antigenicity of collagen (A) was compared with that of collagen (B) and the effect of collagen (B) used as carrier of BMP on ectopic bone formation was compared with that of collagen (C). Namely, collagen (A) was a preparation solubilized without removal of aggregates, collagen (B) was a preparation in which pepsin was still acting after removal of aggregates and collagen (C) was a preparation in which aggregates were removed but pepsin was not acting on collagen after filtration.

Figure 5:
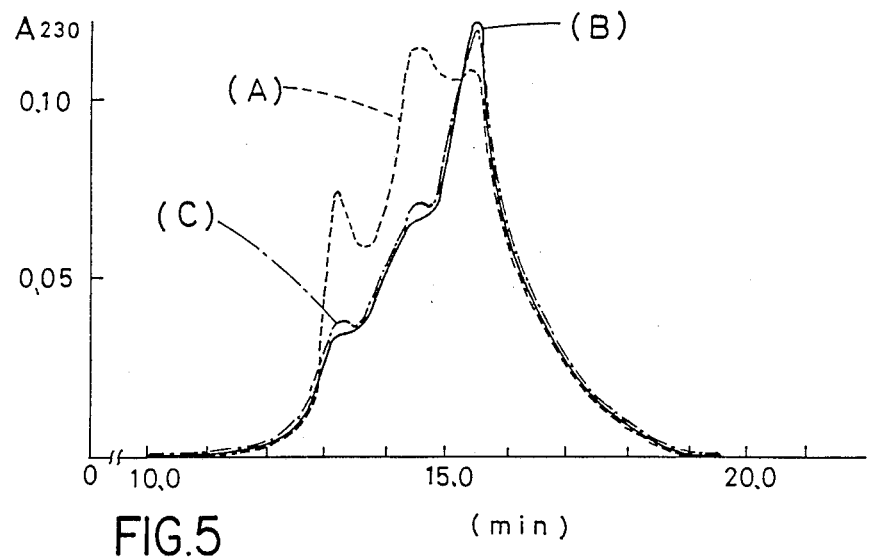
FIG. 5 shows the molecular weight distribution determined by HPLC of 3 kinds of collagen to detect the presence or absence of aggregates.

After each of the above preparations were subjected to denaturation by heating at 50° C for 30 min, the molecular weight distribution was determined by HPLC (high performance liquid chromatography) using TSK Gel (G-4000 PW +G-3000 PW; from Toyo Soda Mfg. Co., Japan). The results are shown in FIG. 5. In the FIGURE the ordinate shows the absorbence $A_{230}$ and abscissa the retention time [min], and the longer the retention time, the smaller is the molecule. The absorbence was measured from the UV absorption at 230 nm. Amino acid analysis was performed by using an amino acid auto-analyzer (K-202 SN: Kyowa Seimitsu Co., Ltd.) after each of the above collagens was hydrolyzed at 110° C. for 24 h and the results are shown in Table 1. Moreover, since tyrosine is considered to be present only in telopeptides of the collagen molecule, the tyrosine content was used as a measure of removal of telopeptides. Namely, on the assumption that tyrosine exists only in telopeptides, 5 tyrosine residues per 1000 residues was regarded as 100% telopeptides existing (not removed at all), the amount of telopeptides was expressed in % and the results are shown in Table 1.

As shown in the molecular weight distribution in FIG. 5, whereas collagen (A) shows a peak at a region of larger molecular weight, collagen (B) exhibits a peak at a region of smaller molecular weight, which suggests removal of aggregates. Collagen (C) subjected to filtration shows a peak similarly at a region of smaller molecular weight. However, the results of amino acid analysis indicate that the tyrosine content in collagen (B) in which pepsin was successively acting after filtration because inactivation was not performed is much lower (smaller than half) than that of in collagen (C) in which pepsin was not acting after filtration. Furthermore, the tyrosine content in collagen (A) is naturally high, as shown in Table 1.

TABLE 1

|  |  |  | Collagen | | |
|---|---|---|---|---|---|
|  |  |  | (A) | (B) | (C) |
| Amino acid composition | Hydroxyproline | HYP | 95.3 | 99.1 | 97.0 |
|  | Aspartic acid | ASP | 42.0 | 44.5 | 44.0 |
|  | Threonine | THR | 17.0 | 16.5 | 17.5 |
|  | Serine | SER | 35.5 | 34.5 | 33.3 |
|  | Glutamic acid | GLU | 72.0 | 71.0 | 70.5 |
|  | Proline | PRO | 118.0 | 112.0 | 116.0 |
|  | Glycine | GLY | 333.0 | 332.4 | 333.9 |
|  | Alanine | ALA | 112.0 | 111.0 | 114.0 |
|  | Cystine | ½CYS | — | — | — |
|  | Valine | VAL | 22.5 | 24.0 | 23.0 |
|  | Methionine | MET | 6.0 | 5.0 | 5.5 |
|  | Isoleucine | ILE | 12.0 | 14.5 | 11.8 |
|  | Leucine | LEU | 28.0 | 30.1 | 27.0 |
|  | Tyrosine | TYR | 3.0 | 1.2 | 2.5 |
|  | Phenylalanine | PHE | 12.6 | 14.0 | 12.5 |
|  | Hydroxylysine | HYL | 9.2 | 8.0 | 8.8 |
|  | Lysine | LYS | 24.0 | 22.7 | 24.2 |
|  | Ammonia | AMM | — | — | — |
|  | Histidine | HIS | 5.6 | 4.8 | 5.5 |
|  | Arginine | ARG | 53.2 | 53.1 | 53.0 |
| Amount of telopeptides (%) |  |  | 60 | 24 | 50 |

Figure 8:
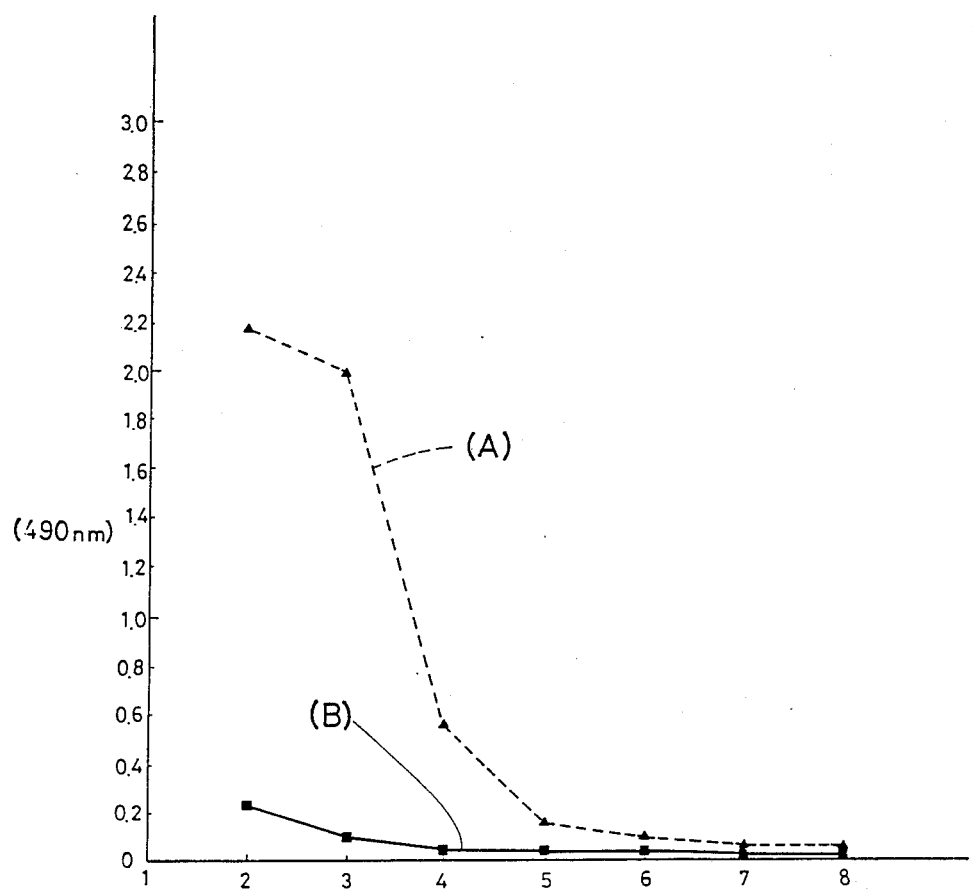
FIG. 8 is a graph indicating the intensity of antigen-antibody reaction with regard to 2 kinds of collagen; we intend to detect the presence or absence of antigenic determinants in this graph.

Meanwhile, the cross reaction of collagen (A) and (B) with collagen antibody was investigated as follows: Namely, polyclonal antibodies to type I collagen ($10^2$- to $10^6$-fold dilutions) was allowed to act on microtiter wells coated with collagen (A) and (B), respectively, and goat antibody to rabbit IgG peroxidase was used as a secondary antibody. Color was developed with O−-phenylenediamine. When collagen reacts with the antibodies to type I collagen (antigen-antibody reaction), O−-phenylene-diamine develops color, so that its absorbence was measured at 490 nm. The value of absorbence means the intensity of antigen-antibody reaction. The results are illustrated in FIG. 8. In the graph the abscissa expresses the common logarithm of dilution of the antibodies to type I collagen on an equally spaced scale, and the ordinate expresses the absorbence at 490 nm on an equally spaced scale. In the FIGURE, a broken line connecting ▲(A) indicates collagen (A) and a broken line connecting ■ (B) is collagen (B). As shown in the FIGURE, when the antibodies to type I collagen of $10^2$-dilution was used, the absorbence (OD value) of collagen (A) was 2.18, but that of collagen (B) was 0.21. Therefore, an antigen-antibody reaction occurs very actively in collagen (A), but such a reaction is hardly found in collagen (B). This is because an antigenic determinant is present in collagen (A) and absent in collagen (B).

Then, the effect of collagen (B) and (C) used as carrier of BMP on ectopic bone formation was investigated as follows: Purified BMP obtained from Dunn osteosarcoma was mixed with each of collagen (B) and (C) solutions, lyophilized and sterilized to give two osteoinductive biomaterials. Each of the biomaterials was implanted into dorsal muscles of mice and after three weeks induction of ectopic bone formation was observed. The biomaterial with collagen (B) was much more effective than one with collagen (C).

From the above results on the tyrosine content, antigenicity and bone formation, a tyrosine content below 2 residues/1000 residues of amino acid is found to serve as a suitable measure for sufficient removal of telopeptides from collagen molecules.

This invention was completed on the basis of the above findings.

Therefore, the present invention includes the tissue-affinitive collagen for osteogenesis characterized by having a tyrosine content below 2 residues/1000 residues of amino acid as the first invention, and a method of producing the tissue-affinitive collagen for osteogenesis formation characterized by using aggregate-removed collagen as raw material and also by making proteolytic enzymes act on this collagen as the second invention.

This invention is explained precisely below.

Collagen is water-insoluble and exists generally in the connective tissues, bones, tendons, and so on of mammalia and so on. Such insoluble collagens are treated and solubilized by, for instance, enzymatic treatment and alkaline treatment and so on. Hitherto, solubilized collagen was purified and sterilized after inactivation of enzyme, and then employed. For this sterilization, a filtration sterilization process where filtration is performed after inactivation as in the case of collagen (C) is often used. However, this filtration sterilization was carried out to remove bacteria and so on, and not to eliminate aggregates of collagen as in this second invention. Namely, filtration of solubilized collagen has not been performed in connection with reduction of antigenicity of collagen hitherto.

In this second invention, aggregate-removed collagen includes the substance whose aggregate content is not always 0, and is obtained, for example, by eliminating collagen aggregates (not always perfectly) through filtration after collagen has been solubilized, as the above, As the filter for this filtration, for example, a membrane filters can be given, but the filter is not restricted to the above one. As the pore size, 3 μm and below are desirable and 0.45 μm or below is more desirable, according to the confirmation by the inventors, but is not restricted to this range. To obtain aggregate-removed collagen, other methods, such as ultracentrifugation of solubilized collagen can be used instead of filtration. Furthermore, since filters with pore size of 0.45 μm or below are often used in producing commercial collagen subjected to filtration sterilization, proteolytic enzymes can be made to act on such collagen, as it is, as collagen from which aggregates are removed.

Meanwhile, aggregates may sometimes have been removed even from commercial collagen depending on the production conditions, such as the extent of filtration sterilization. Thus, we performed experiments similar to the above ones to know whether such collagen can be used as aggregate-removed collagen. Namely, a commercial collagen, Vitrogen-100 (Collagen Corp. U. S. A.) (D), and the product obtained by treating this collagen with pepsin (E) were used for the measurement of molecular weight distribution and the amino acid analysis similarly to the above experiments. Moreover, the amount of telopeptides was examined similarly.

Figure 6:
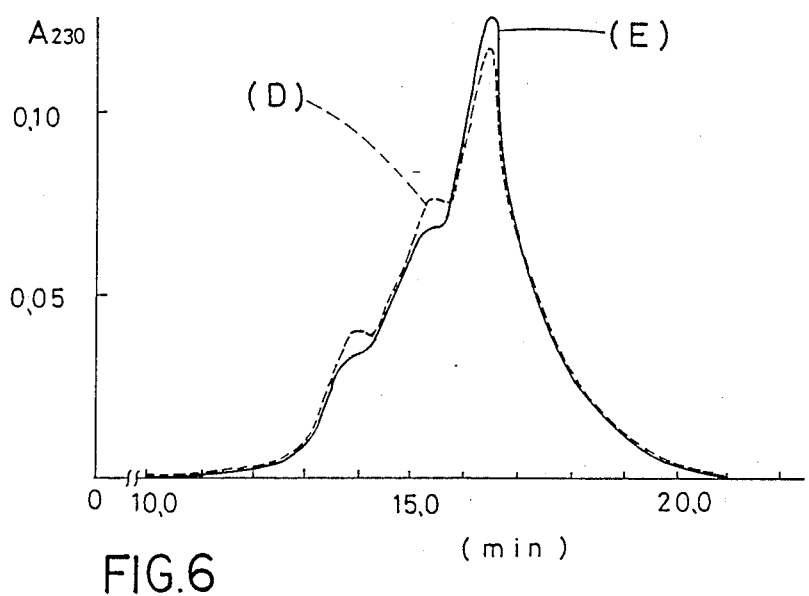
FIG. 6 represents the molecular weight distribution of commercial collagen by HPLC to detect the presence or absence of aggregates.

The results of measurement of molecular weight distribution are shown in FIG. 6. In FIG. 6 the ordinate shows the absorbence $A_{230}$ and the abscissa expresses the retention time [min], and the longer the retention time is, the smaller is the molecular weight. The absorbence was measured in UV absorption at 230 nm. The results of amino acid analysis and the amount of telopeptides are shown in Table 2.

TABLE 2

| | | | Collagen | |
|---|---|---|---|---|
| | | | (D) | (E) |
| Amino acid composition | Hydroxyproline | HYP | 96.0 | 98.4 |
| | Aspartic acid | ASP | 41.5 | 42.3 |
| | Threonine | THR | 16.7 | 17.0 |
| | Serine | SER | 36.0 | 35.4 |
| | Glutamic acid | GLU | 73.0 | 72.5 |
| | Proline | PRO | 119.2 | 118.5 |
| | Glycine | GLY | 335.1 | 341.4 |
| | Alanine | ALA | 114.5 | 113.7 |
| | Cystine | ½ CYS | — | — |
| | Valine | VAL | 18.0 | 17.5 |
| | Methionine | MET | 5.3 | 5.6 |
| | Isoleucine | ILE | 10.5 | 11.0 |
| | Leucine | LEU | 24.0 | 26.5 |
| | Tyrosine | TYR | 2.3 | 1.1 |
| | Phenylalanine | PHE | 11.8 | 12.8 |
| | Hydroxylysine | HYL | 8.3 | 8.2 |
| | Lysine | LYS | 22.4 | 23.9 |
| | Ammonia | AMM | — | — |
| | Histidine | HIS | 4.1 | 4.2 |
| | Arginine | ARG | 49.9 | 50.0 |
| Amount of telopeptides (%) | | | 46 | 22 |

As seen in FIG. 6, the molecular weight distribution of the commercial collagen (D) is similar to that of (C) in FIG. 5, and the distribution of product obtained by treating the collagen with pepsin (E) was similar to that of (B) in FIG. 5. Moreover, as seen in Table 2, the tyrosine content of collagen (E) was much smaller than that of the original collagen (D). Therefore, the amount of telopeptides which becomes the cause of antigenicity is less and the telopeptides are found to be nearly completely removed in collagen (E).

As seen in the above results, some commercial collagen can yield tissue-affinitive collagen for osteogenesis when the former is used as it is, as aggregate-removed collagen and a proteolytic enzyme is made to act on it, in accordance with the method of this invention. Aggregate-removed collagen may also be obtained by filtration and ultracentrifugation and so on of other commercial collagens.

In the present invention the tyrosine content is used as the measure of telopeptides removal from collagen molecules. This is because tyrosine is considered to be present only in telopeptides of collagen molecules, as stated above. When tyrosine exists below 2 residues/1000 residues of amino acid, telopeptides are sufficiently removed from collagen and the resultant collagen has hardly or no antigenicity. When the tyrosine content is 1.5 residues/1000 residues or below, the case is more favorable from the viewpoint of reduction of antigenicity.

Furthermore, the tissue-affinitive collagen for bone formation to be used in the first invention may be obtained by a production method other than the one defined by the second invention. For example, it is known that alkali-solubilized collagen, which is obtained by treating collagen with approximately 5%-NaOH solution in the presence of saturated $Na_2SO_4$, contains a very low content of telopeptides.

Using aggregate-removed collagen as raw material in this second invention is for proteolytic enzymes to be made easier to act on the telopeptides of the collagen molecule.

To make proteolytic enzymes act on aggregate-removed collagen, proteolytic enzymes are added to collagen in which aggregates have been removed. Alternatively, when proteolytic enzymes are not inactivated on filtrating collagen solubilized as the above, proteolytic enzymes, as it is, act on the collagen in the filtrate. In the collagen subjected to treatment with proteolytic enzymes, the telopeptides has been eliminated readily (not always completely removed) and the antigenicity is very low. Therefore, foreign substance reactions also do not occur at all and further the tissue affinity is very good.

The tissue-affinitive collagen for osteogenesis of this invention can be mixed with BMP arbitrarily, remains undissolved in the living body for the period till osteogenesis (for example, for 2 weeks) and permits bone induction to occur smoothly.

Moreover, it is desirable that the isoelectric point of the tissue-affinitive collagen for osteogenesis of this invention lies at 7 or above. This intends to give collagen a property that it remains undissolved under physiological conditions, namely when implanted, for some time (for instance, for the period till osteogenesis). Moreover, when the tissue-affinitive collagen for osteogenesis of the present invention is obtained by alkali-treatment, the isoelectric point may be lower than 7, and formability may be inferior to that obtained by enzyme-treatment. Therefore, it is desirable to obtain the tissue-affinitive collagen for osteogenesis of this invention by enzyme-treatment.

Table 3 summarizes the examples of form of usage and uses of tissue-affinitive collagen for osteogenesis of the first invention, but they are not restricted to the above matters.

TABLE 3

| Aim of use | Form of usage | Uses |
| --- | --- | --- |
| Osteogenesis | In solid (in mass or tape) with BMP | Filling and repair of bone defects |
| | With BMP in coating artificial bones and joints | Adhesion of an artificial bone and joint to a living bone |
| | With BMP in tape in covering artificial bones and joints | Adhesion of an artificial bone and joint to a living bone |

Moreover, the bone morphogenic proteins mentioned here are substances which act on undifferentiated mesenchymatous cells from the outside of cells and induce their genetic characters to the chondrocytes and osteoblasts (cartilage induction, bone induction). An example of method to produce it is shown below, but the methods are not restricted to this.

An example of preparation method of bone morphogenic proteins

Figure 7:
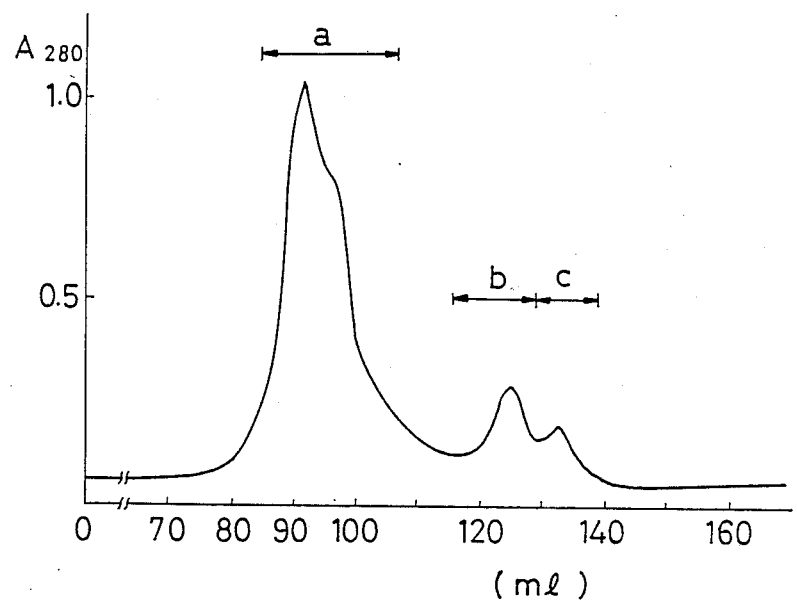
FIG. 7 illustrates an elusion curve produced by chromatography to obtain bone morphogenic protein.

Dunn osteosarcoma is homogenized, defatted with acetone and methyl ether, the resultant substance is dried and a defatted and dried powder of osterosarcoma is obtained. Next, the defatted and dried powder is extracted with 4 M guanidine hydrochloride, ethanol fractionation is performed with ethanol containing 4% acetic acid, the supernatant of the fraction is dialyzed against 10 mM sodium phosphate buffer (pH 7.4). When the solution is dialyzed thoroughly, a precipitate appears in the tube, which is recovered by centrifugation (10000 G, 15 min) and the supernatant is discarded. The recovered precipitate fraction is dissolved again in guanidine hydrochloride. Next, chromatography is performed through gel filtration and so on. FIG. 7 is the elusion pattern obtained when chromatography is performed through Sephacryl S-200 gel (Pharmacia Fine Chemicals). In the FIGURE the ordinate shows absorbence A280 and the abscissa elution volume [ml]. The absorbence is measured in UV absorption at 280 nm. The fraction b shown in FIG. 7 is recovered and dialyzed against 10 mM sodium phosphate buffer and the deposit is recovered by centrifugation (1000G, 15 min), purified, lyophilized BMP are obtained.

Next, examples of biomaterials in which tissue-affinitive collagen for osteogenesis of this first invention is used together with the above BMP are shown, but application of this collagen is not restricted to these examples.

EXAMPLE 1

Fresh calf skin was dehaired, cleaned by shaving, cut into small pieces, washed with NaCl solution and water, and then defatted with a mixture of methanol and chloroform. The purified skin was added to a HCl solution, and the mixture was adjusted to pH 3.0 with HCl and added pepsin (approximate ratio of pepsin to collagen is 4/100). The mixture was kept at 20° C for 24 h with occasional stirring and then filtered with a glass filter and subsequently with a nitrocellulose membrane filter with a pore size of 0.45 μm, and the filtrate was further kept at 20° C for 24 h. The resulting solution was then adjusted to pH 10.0 with NaOH to inactivate pepsin and readjusted to pH 7.4 with HCl, and the collagen precipitate was collected by centrifuging and dissolved in a HCl solution, pH 3.0. Next, the 1/5 volume of a 30% NaCl solution was added to the solution and the resulting precipitate was collected and dispersed in a HCl solution, pH 3.0. The dispersion was dialyzed exhaustively against HCl solution, pH 3.0 and the solution was again adjusted to pH 7.4 with NaOH. The collagen precipitate was collected and then dissolved in a HCl solution, pH 3.0 to give a collagen solution with a concentration of 3 mg/ml. The tyrosine content of the collagen was 1.2 residues/ 1,000 residues and the isoelectric point was above 7.

Purified BMP obtained by the above-mentioned method was dissolved in a HCl solution, pH 3.0 at a concentration of 3.0 mg/ml. One hundred (100) ||1 of the solution was mixed well with 1.0 ml of the collagen solution and the mixture was adjusted to pH 7.4 with NaOH, lyophilized, and then sterilized with ethylene oxide gas to give an osteoinductive biomaterial.

Figure 1:
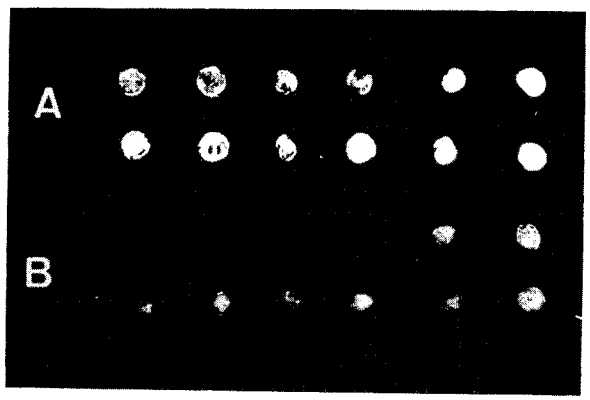
FIG. 1 is an X-ray film showing the state of bone induction of biomaterials implanted into mice . In A collagen described in Example 1 was used, and collagen stated in Reference example 1 was employed in B.
Figure 4:
FIGS. 2 to 4 are photos showing biological morphology.
Figure 2:
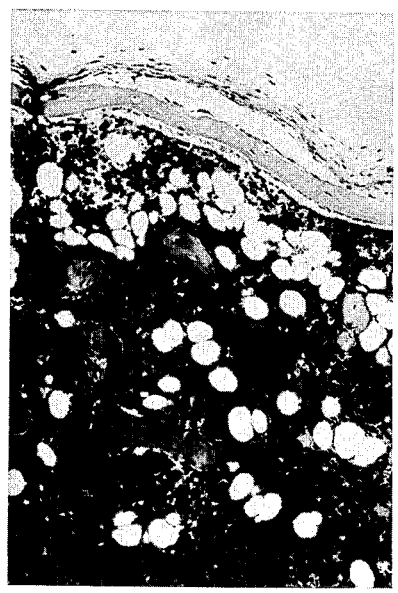

This biomaterial was implanted into dorsal muscles of mice, the graft (shown with an arrow in FIG. 4) was taken out after 3 weeks and a soft X ray film was taken, which was shown in FIG. 1A. In FIG. 1A the white part was the bone matrix (trabecule). As shown in the photo of FIG. 1A, the biomaterial using tissue-affinitive collagen for osteogenesis of this invention induced bone tissues very well in all the 12 samples. The fluctuations between the samples were also small. FIG. 2 shows a magnification photo of a part of tissue from the graft taken out.

In the photo of FIG. 2 a gray belt extending to the right and left in the upper part is the bone matrix (trabecule), black spots in this bone matrix are osteocytes, a stripe above the bone matrix is a muscle and the part below the muscle is the graft. In the graft white large spot-like parts are fat cells, large gray parts are the bone matrices (trabecule) and many black spots between the bone matrices are the myeloid cells (hemopoietic cells). Black spots in this matrix are osteocytes and black parts at the margin of the bone matrix are osteoblasts.

As shown in FIG. 2, when the above biomaterial was implanted into dorsal muscles of mice, bone tissues were formed in the graft after 3 weeks.

According to the observations of the inventors, the process of formation of the bone tissues was as follows:

When the above biomaterial was implanted into dorsal muscles of mice, undifferentiated cells which seemed to have migrated out of the muscles appeared at the contact surface of the margin of graft with the muscle near the collagen fibril after 4 days. One week after the transplantation a cartilage was formed at the contact surface of the margin of graft with the muscle. After 2 weeks vessels advanced into the cartilage formed, and absorption of cartilage matrix and addition of new bone to the matrix were able to be seen. As the result, a trabecule with a cartilaginous core (primary trabecule) was formed. Bone marrow tissues appeared in the space between these trabecules and this process advanced from the margin to the central part of the graft. Three weeks after the transplantation this process advanced to the central part of graft and bone tissues observed in FIG. 2 were formed.

Meanwhile, the quantitative osteogenetic ability was investigated using the $^{85}$sSr uptake method as follows: After the above biomaterial was implanted into dorsal muscles of mice, 10000 cpm of $^{85}$Sr was injected intraperitonealy into the animal. After 3 weeks the graft was taken out and the amount of $^{85}$Sr uptake in the graft was determined with a Y-ray counter; the amount was found to be 2116±790 cpm. This suggested a very good osteogenesis together with the above X-ray film (soft X-ray film) and the findings of bone tissue formation.

EXAMPLE 2

A collagen solution was prepared in the same manner mentioned in Example 1 except using a membrane filter with a pore size of 3.0 μm instead of 0.45 μm filter and the collagen had a tyrosine content of 2.0 residues/1,000 residues and an isoelectric point of above 7. Next, an osteoinductive biomaterial was obtained using the collagen solution and implanted according to Example 1. The results were almost same as those in Example 1.

REFERENCE EXAMPLE 1

Fresh calf skin was dehaired, cleaned by shaving, cut into small pieces, washed with NaCl solution and water, and then defatted with a mixture of methanol and chloroform. The purified skin was added to a HCl solution, and the mixture was adjusted to pH 3.0 with HCl and added pepsin (approximate ratio of pepsin to collagen is 4/100). The mixture was kept at 20° C. for 48 h, filtered with a glass filter, then adjusted to pH 10.0 to inactivate pepsin and filtered with a membrane filter with a pore size of 0.45 μm. The filtrate was then treated similar to Example 1 to give a collagen solution and the collagen had a tyrosine content of 2.5 residues/1,000 residues and an isoelectric point of above 7.

Next, an osteoinductive biomaterial was prepared using the collagen solution and implanted according to Example 1. The graft was taken out after 3 weeks, and the results were shown in FIG. 1B. In FIG. 1B bone induction occurs in the white part. As seen in the photo of FIG. 1B, the biomaterial thus obtained shows a slight induction of bone tissues in 5 of 12 samples, but did not in some samples; fluctuations in bone induction were large between samples. A magnification photo of a part of tissue from the graft taken out is shown in FIG. 3.

Figure 3:
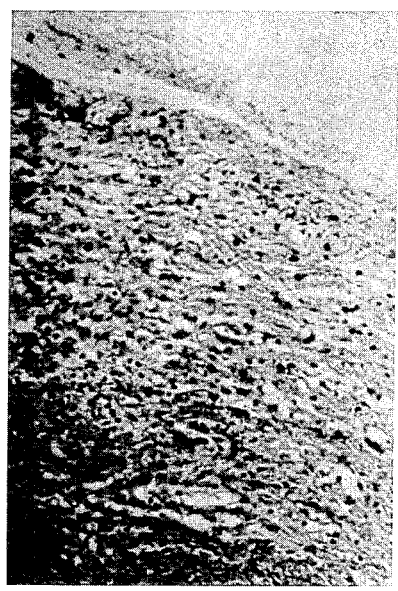

In FIG. 3, a white belt extends to the right and left in the upper part. The part above the belt is a muscle and the part below the belt is a graft. The gray fibers in the part of graft are collagen fibrils. As found in this photo, bone is not induced.

Furthermore, the $^{85}$Sr uptake was investigated similar to Example 1 and the amount was 963±371 cpm, which suggests poor osteogenesis together with the above X-ray film (soft X-ray film) and results of formation of bone tissues.

Next, standard and reference examples using commercial collagen in which removal of aggregates is confirmed are stated.

EXAMPLE 3

A commercial collagen solution (pH 2.5; concentration 3.0 mg/ml), Vitrogen-100 (Collagen Corp. U. S. A.) of which the molecular distribution and amino acid composition were mentioned above, was used. The solution was added pepsin (ratio of pepsin to collagen is 2/100), kept at 20° C for 24 h, adjusted to pH 10.0 with NaOH to inactivate pepsin and then treated similar to Example 1 to give a collagen solution (3 mg/ml). The tyrosine content of the collagen was 1.1 residues/1,000 residues and the isoelectric point was above 7. An osteoinductive biomaterial was prepared using the collagen solution and implanted according to Example 1. After 3 weeks, very good induction of bone tissue was observed.

REFERENCE EXAMPLE 2

The commercial collagen solution used in Example 3 (tyrosine content 2.3 residues/1,000 residues; isoelectric point above 7) was mixed with BMP to give an osteoinductive biomaterial, which was implanted in mice according to Example 1. After 3 weeks, bone tissue was little induced in the graft.

Next, standard example showing that when tissue-affinitive collagen for osteogenesis of this invention is used, bone induction occurs smoothly, and its reference example are stated.

EXAMPLE 4 and REFERENCE EXAMPLE 3

Four (4) kinds of osteoinductive biomaterial using the collagen solution obtained in Example 1 and the BMP solution mentioned above were prepared by mixing 0.75, 0.30, 0.19 and 0.094 mg of BMP, respectively, with 3 mg of collagen according to the procedure in Example 1. Each of the 4 biomaterials was implanted in mice and the osteogenesis and the $^{85}$Sr uptake were investigated according to Example 1. At the same time sole implantation of BMP was investigated. The results are shown in Table 4.

TABLE 4

| | Biomaterial | | | Amount of $^{85}$Sr intake (cmp) (mean ± standard deviation) | Amount of $^{85}$Sr uptake (cmp/mg-BMP) (mean ± standard deviation) |
|---|---|---|---|---|---|
| | BMP (mg) | Tissue-affinitive collagen (mg) | Osteogenesis Present ... o Absent ... x | | |
| Example 4 | 0.75 | 3 | o | 2535 ± 403 | 3380 ± 537 |
| | 0.30 | 3 | o | 2147 ± 644 | 7157 ± 845 |
| | 0.19 | 3 | o | 1241 ± 266 | 6532 ± 607 |
| | 0.094 | 3 | o | 569 ± 98 | 6053 ± 771 |
| Reference | 1.20 | — | x | 85 ± 10 | — |
| example 3 | 6.00 | — | o | 806 ± 210 | 134 ± 35 |

As shown in Table 4, when BMP alone was used, osteogenesis was not found at an amount of 1.20 mg and when a large amount of BMP, 6.00 mg, was used the amount of $^{85}$Sr uptake was small with 806 cpm, which indicated insufficient bone induction. In contrast, when BMP was used for biomaterial, mixed with tissue-affinitive collagen for osteogenesis of this invention, osteogenesis was able to be observed even when the amount of BMP was very small with a value of 0.094 mg. Thus, when mixed with this tissue-affinitive collagen, bones were able to be formed very well, even when the amount of BMP was considerably smaller than that used in the case of single use when osteogenesis was not observed. Namely, bone induction was found to occur smoothly when tissue-affinitive collagen for osteogenesis of this invention was used combined.

EXAMPLE 5

Purified, calf skin (500 g) obtained according to Example 1 was treated in one liter of a 5% NaOH solution containing 16% Na$_2$SO$_4$ at 20° C for 5 days with occasional stirring. The resulting skin was neutralized to pH approximately 7 with HCl, washed thoroughly with water, dissolved in a HCl solution, pH 3.0, and then filtered with a glass filter to remove insoluble material. Sodium chloride was added to the filtrate at a final concentration of 7% to precipitate collagen, the precipitate was collected by centrifuging, then dispersed in a HCl solution, pH 3.0, and dialyzed exhaustively against sufficient amounts of HCl solution, pH 3.0. The collagen concentration of the dyalyzate was adjusted with the HCl solution to give an alkali-solubilized collagen solution with a concentration of 3 mg/ml, and the collagen had a tyrosine content of 0.9 residues/1,000 residues, and had an isoelectric point of below 6.

A biomaterial was prepared using the collagen solution and the purified BMP and implanted into dorsal muscles of mice in the same manner described in Example 1. As the result, osteogenesis was almost similar to in Example 1, but the bone tissues induced were spread out and not maintained the shape of the biomaterial implanted.

From the above results, tissue-affinitive collagen for osteogenesis related to this first invention is shown to have no antigenecity and have a very good tissue affinity compared with conventional collagen. Therefore, this tissue-affinitive collagen is found to become an excellent medical material and biomaterial. And it is found to be desirable that the isoelectric point of the tissue-affinitive collagen for osteogenesis of this invention lies at 7 or above.

Since the tissue-affinitive collagen for osteogenesis related with the first invention has, as the above, tyrosine content below 2 residues/1000 residues, telopeptides attributable to antigenicity are sufficiently eliminated. The tissue-affinitive collagen for osteogenesis in this invention has a very good tissue-affinity without antigenicity compared with conventional collagens, so that bone formation occurs smoothly when this collagen is used as the carrier of BMP. Furthermore, reproducibility of bone formation is very good and bone morphogenesis is induced smoothly with a small amount of BMP.

Since the production method of the tissue-affinitive collagen for osteogenesis related with the second invention uses, as the above, aggregate-removed collagen as raw material and makes proteolytic enzymes to act on the collagen to obtain the tissue-affinitive collagen for osteogenesis having a tyrosine content below 2 residues/1000 residues, the tissue-affinitive collagen for osteogenesis related with the first invention can be readily obtained. Moreover, the tissue-affinitive collagen for osteogenesis obtained by this production method has become soluble with difficulty under physiological conditions.

I claim:

1. Collagen for use as a carrier of bone morphogenic protein for osteogenesis which is a tissue-affinitive Type I collagen obtained from animals characterized by a tyrosine content of 1.5 residues/1000 residues or less, a minimum serine content of 10.0 residues/1000 residues, an isoelectric point of 7 or higher, and which is substantially free of aggregates.

2. A process for producing a tissue-affinitive collagen for use as a carrier of bone morphogenic protein for osteogenesis which is a tissue-affinitive Type I collagen obtained from animals, characterized by a tyrosine content of 1.5 residues/1000 residues or less, an isoelectric point of 7 or higher, and which is substantially free of aggregates which process comprises removing aggregates from solubilized collagen by filtration and subjecting the obtained collagen to the action of proteolytic enzymes after filtration and subsequently deactivating the proteolytic enzymes.

3. A process according to claim 2, wherein the collagen is subjected to the action of proteolytic enzymes at a temperature below the inactivation temperature of said enzyme and the denaturation temperature of said collagen.

* * * * *